(12) United States Patent
Lippert et al.

(10) Patent No.: US 10,953,202 B2
(45) Date of Patent: Mar. 23, 2021

(54) GUIDEWIRE DEVICES HAVING DISTALLY EXTENDING COILS AND SHAPEABLE TIPS

(71) Applicant: SCIENTIA VASCULAR, West Valley City, UT (US)

(72) Inventors: John A. Lippert, Park City, UT (US); Edward J. Snyder, Park City, UT (US)

(73) Assignee: SCIENTIA VASCULAR, LLC, West Valley City, UT (US)

( * ) Notice: Subject to any disclaimer, the term of this patent is extended or adjusted under 35 U.S.C. 154(b) by 0 days.

(21) Appl. No.: 15/611,328

(22) Filed: Jun. 1, 2017

(65) Prior Publication Data
US 2018/0015262 A1 Jan. 18, 2018

Related U.S. Application Data

(60) Provisional application No. 62/363,760, filed on Jul. 18, 2016.

(51) Int. Cl.
*A61B 5/00* (2006.01)
*A61M 25/09* (2006.01)
(Continued)

(52) U.S. Cl.
CPC .......... *A61M 25/09* (2013.01); *A61L 31/022* (2013.01); *A61L 31/18* (2013.01);
(Continued)

(58) Field of Classification Search
CPC ...... A61M 25/0147; A61M 2025/1081; A61M 25/0054; A61M 25/0105; A61M 2025/1093; A61M 25/0023; A61M 25/0068; A61M 25/01; A61M 25/0138; A61M 25/0141; A61M 25/0662; A61M 25/09; A61B 17/12109; A61B 17/00234;
(Continued)

(56) References Cited

U.S. PATENT DOCUMENTS 2,022,065 A 11/1935 Wappler
2,187,299 A 1/1940 Burkhardt
(Continued)

FOREIGN PATENT DOCUMENTS

AU 7230740 11/1997
AU 733966 5/2001
(Continued)

OTHER PUBLICATIONS

Canadian Office Action for CA2757655 dated Jan. 2, 2018.
(Continued)

*Primary Examiner* — May A Abouelela
(74) *Attorney, Agent, or Firm* — Workman Nydegger

(57) ABSTRACT

The present disclosure relates to guidewire devices having shapeable tips and effective torquability. A guidewire device includes a core having a proximal section and a tapered distal section. A tube structure is coupled to the core such that the tapered distal section of the core extends into and distally beyond the tube structure. The portion of the core extending distally beyond the tube forms a shapeable tip. One or more coils also extend distally beyond the tube. The tip is configured to reduce the tendency of resilient forces from the tube structure to disrupt a customized shape of the tip.

21 Claims, 6 Drawing Sheets

(51) Int. Cl.
*A61L 31/02* (2006.01)
*A61L 31/18* (2006.01)
*A61M 25/00* (2006.01)

(52) U.S. Cl.
CPC . *A61M 25/0051* (2013.01); *A61M 2025/0915* (2013.01); *A61M 2025/09075* (2013.01); *A61M 2025/09083* (2013.01); *A61M 2025/09091* (2013.01); *A61M 2025/09133* (2013.01); *A61M 2025/09141* (2013.01); *A61M 2025/09166* (2013.01); *A61M 2025/09175* (2013.01)

(58) Field of Classification Search
CPC ............ A61B 2090/3966; A61B 90/39; A61B 17/1214; A61B 2017/00778
USPC .......................................... 600/585; 604/523
See application file for complete search history.

(56) References Cited

U.S. PATENT DOCUMENTS

| | | |
|---|---|---|
| 3,183,702 A | 5/1965 | Zittel |
| 3,572,334 A | 3/1971 | Petterson |
| 3,612,058 A | 10/1971 | Ackerman |
| 3,709,271 A | 1/1973 | Flory |
| 3,920,058 A | 11/1975 | Walker |
| 4,163,406 A | 8/1979 | Crawford |
| 4,239,069 A | 12/1980 | Zimmerman |
| 4,416,312 A | 11/1983 | Ostberg |
| 4,688,540 A | 8/1987 | Ono |
| 4,719,924 A | 1/1988 | Crittenden |
| 4,846,186 A | 7/1989 | Box |
| 4,895,168 A | 1/1990 | Machek |
| 4,989,608 A | 2/1991 | Ratner |
| 5,047,045 A | 9/1991 | Arney et al. |
| 5,069,217 A | 12/1991 | Fleischhacker |
| 5,084,022 A | 1/1992 | Claude |
| 5,095,915 A | 3/1992 | Angelson |
| 5,102,390 A | 4/1992 | Crittenden et al. |
| 5,147,317 A | 9/1992 | Shank |
| 5,154,725 A | 10/1992 | Leopold |
| 5,174,302 A | 12/1992 | Palmer |
| 5,315,996 A | 5/1994 | Lundquist |
| 5,326,374 A | 7/1994 | Ilbawi et al. |
| 5,345,945 A * | 9/1994 | Hodgson ......... A61M 25/09033 600/433 |
| 5,372,587 A | 12/1994 | Hammerslag |
| 5,382,259 A | 1/1995 | Phelps |
| 5,385,152 A | 1/1995 | Abele |
| 5,437,288 A | 8/1995 | Schwartz |
| 5,441,483 A | 8/1995 | Avitall |
| 5,506,682 A | 4/1996 | Pryor |
| 5,507,751 A | 4/1996 | Goode et al. |
| 5,551,444 A | 9/1996 | Finlayson |
| 5,554,114 A | 9/1996 | Wallace et al. |
| 5,569,218 A | 10/1996 | Berg |
| 5,573,520 A | 11/1996 | Schwartz |
| 5,573,867 A | 11/1996 | Zafred et al. |
| 5,659,205 A | 8/1997 | Weisser |
| 5,673,707 A | 10/1997 | Chandrasekaran |
| 5,676,659 A | 10/1997 | McGurk |
| 5,685,568 A | 11/1997 | Pirrello |
| 5,685,868 A | 11/1997 | Lundquist |
| 5,690,120 A | 11/1997 | Jacobsen |
| 5,706,826 A * | 1/1998 | Schwager ............ A61M 25/09 600/585 |
| 5,741,429 A | 4/1998 | Donadio |
| 5,746,701 A | 5/1998 | Noone |
| 5,792,154 A | 8/1998 | Doan |
| 5,800,454 A | 9/1998 | Jacobsen |
| 5,833,631 A | 11/1998 | Nguyen |
| 5,833,632 A | 11/1998 | Jacobsen |
| 5,842,461 A | 12/1998 | Azuma |
| 5,860,963 A | 1/1999 | Azam |
| 5,876,356 A | 3/1999 | Viera et al. |
| 5,911,715 A | 6/1999 | Berg |
| 5,911,717 A | 6/1999 | Jacobsen |
| 5,916,194 A | 6/1999 | Jacobsen |
| 5,931,830 A | 8/1999 | Jacobsen |
| 5,954,672 A * | 9/1999 | Schwager ............ A61B 5/6851 600/585 |
| 6,004,279 A | 12/1999 | Crowley |
| 6,014,919 A | 1/2000 | Jacobsen |
| 6,017,319 A | 1/2000 | Jacobsen |
| 6,022,343 A | 2/2000 | Johnson et al. |
| 6,022,369 A | 2/2000 | Jacobsen |
| 6,027,863 A | 2/2000 | Donadis |
| 6,033,288 A | 3/2000 | Weisshaus |
| 6,033,394 A | 3/2000 | Vidlund |
| 6,056,702 A | 5/2000 | Lorenzo |
| 6,063,101 A | 5/2000 | Jacobsen |
| 6,110,164 A | 8/2000 | Vidlund |
| 6,132,389 A | 10/2000 | Cornish |
| 6,139,511 A | 10/2000 | Huter |
| 6,168,570 B1 | 1/2001 | Ferrera |
| 6,179,828 B1 | 1/2001 | Mottola |
| 6,183,410 B1 | 2/2001 | Jacobsen |
| 6,183,420 B1 * | 2/2001 | Douk .................... A61M 25/09 600/434 |
| 6,214,042 B1 | 4/2001 | Jacobsen |
| 6,228,073 B1 | 5/2001 | Noone |
| 6,245,030 B1 | 6/2001 | Dubois |
| 6,251,086 B1 | 6/2001 | Cornelius |
| 6,260,458 B1 | 7/2001 | Jacobsen |
| 6,261,246 B1 | 7/2001 | Pantages et al. |
| 6,273,881 B1 | 8/2001 | Kiemeneij |
| 6,302,870 B1 | 10/2001 | Jacobsen |
| 6,306,105 B1 | 10/2001 | Rooney |
| 6,346,091 B1 * | 2/2002 | Jacobsen .......... A61B 17/12022 604/508 |
| 6,356,791 B1 | 3/2002 | Westlund |
| 6,402,706 B2 | 6/2002 | Richardson et al. |
| 6,428,489 B1 * | 8/2002 | Jacobsen ............ A61M 25/0054 600/585 |
| 6,431,039 B1 | 8/2002 | Jacobsen |
| 6,436,056 B1 | 8/2002 | Wang et al. |
| 6,440,088 B1 | 8/2002 | Jacobsen |
| 6,458,867 B1 | 10/2002 | Wang et al. |
| 6,464,651 B1 | 10/2002 | Hiejima et al. |
| 6,492,615 B1 | 12/2002 | Flanagan |
| 6,494,894 B2 | 12/2002 | Mirarchi |
| 6,527,732 B1 | 3/2003 | Strauss |
| 6,527,746 B1 | 3/2003 | Oslund |
| 6,553,880 B2 | 4/2003 | Jacobsen |
| 6,554,820 B1 | 4/2003 | Wendlandt |
| 6,558,355 B1 | 5/2003 | Metzger |
| 6,579,246 B2 | 6/2003 | Jacobsen |
| 6,602,207 B1 | 8/2003 | Mam |
| 6,606,985 B2 | 8/2003 | Negishi |
| 6,610,046 B1 | 8/2003 | Usami et al. |
| 6,652,508 B2 | 11/2003 | Griffin |
| 6,671,560 B2 | 12/2003 | Westlund |
| 6,766,720 B1 | 7/2004 | Jacobsen |
| 6,805,676 B2 | 10/2004 | Klint |
| RE39,018 E | 3/2006 | Azuma |
| 7,024,885 B2 | 4/2006 | Villalobos |
| 7,097,624 B2 | 8/2006 | Campion |
| 7,110,910 B1 | 9/2006 | Deffenbaugh |
| 7,182,735 B2 * | 2/2007 | Shireman ............... A61M 25/09 600/585 |
| 7,276,062 B2 | 10/2007 | McDaniel et al. |
| 7,338,345 B2 | 3/2008 | Fujinami |
| 7,421,929 B2 | 9/2008 | French |
| 7,494,474 B2 | 2/2009 | Richardson et al. |
| 7,621,880 B2 | 11/2009 | Ryan |
| 7,637,875 B2 | 12/2009 | Itou |
| 7,641,622 B2 | 1/2010 | Satou |
| 7,670,302 B2 | 3/2010 | Griffin |
| 7,699,792 B2 | 4/2010 | Hofmann |
| 7,722,545 B2 | 5/2010 | Bertsch |
| 7,722,552 B2 | 5/2010 | Aimi |
| 7,744,545 B2 | 6/2010 | Aimi |
| 7,747,314 B2 | 6/2010 | Parins |

(56) References Cited

U.S. PATENT DOCUMENTS

| | | |
|---|---|---|
| 7,753,859 B2 | 7/2010 | Kinoshita |
| 7,766,896 B2 | 8/2010 | Volk |
| 7,769,839 B2 | 8/2010 | Boivie et al. |
| 7,785,273 B2 * | 8/2010 | Eskuri .................. A61M 25/09 600/585 |
| 7,789,839 B2 | 9/2010 | Lupton |
| 7,806,837 B2 | 10/2010 | Rasmussen |
| 7,878,984 B2 | 2/2011 | Davis |
| 7,883,474 B1 | 2/2011 | Mirigian |
| 7,914,467 B2 | 3/2011 | Layman et al. |
| 7,942,832 B2 | 5/2011 | Kanuka |
| 7,989,042 B2 | 8/2011 | Obara et al. |
| 8,043,314 B2 | 10/2011 | Noriega et al. |
| 8,048,004 B2 | 11/2011 | Davis et al. |
| 8,105,246 B2 | 1/2012 | Voeller |
| 8,128,579 B2 | 3/2012 | Chen |
| 8,128,580 B2 | 3/2012 | Fujimagari |
| 8,137,293 B2 | 3/2012 | Zhou |
| 8,167,821 B2 | 5/2012 | Sharrow et al. |
| 8,257,279 B2 | 9/2012 | Jacobsen |
| 8,292,828 B2 | 10/2012 | Uihlein |
| 8,357,140 B2 | 1/2013 | Majercak |
| 8,376,961 B2 | 2/2013 | Layman |
| 8,377,056 B2 | 2/2013 | Oyola et al. |
| 8,409,114 B2 | 4/2013 | Parins |
| 8,444,577 B2 | 5/2013 | Bunch |
| 8,454,535 B2 | 6/2013 | Majercak |
| 8,460,213 B2 | 6/2013 | Northrop |
| 8,468,919 B2 | 6/2013 | Christian |
| 8,500,658 B2 | 8/2013 | Boyle |
| 8,517,959 B2 | 8/2013 | Kurosawa |
| 8,535,243 B2 | 9/2013 | Shireman |
| 8,540,648 B2 | 9/2013 | Uihlein |
| 8,551,020 B2 | 10/2013 | Chen et al. |
| 8,551,021 B2 | 10/2013 | Voeller |
| 8,622,931 B2 | 1/2014 | Teague |
| 8,622,933 B2 | 1/2014 | Maki |
| 8,758,269 B2 * | 6/2014 | Miyata .................. A61M 25/09 600/585 |
| 8,795,202 B2 | 8/2014 | Northrop |
| 8,795,254 B2 | 8/2014 | Layman |
| 8,821,477 B2 | 9/2014 | Northrop |
| 8,870,790 B2 | 10/2014 | Jacobsen |
| 8,900,163 B2 | 12/2014 | Jacobsen |
| 8,915,865 B2 | 12/2014 | Jacobsen et al. |
| 8,932,235 B2 | 1/2015 | Jacobsen |
| 8,936,558 B2 | 1/2015 | Jacobsen |
| 8,939,916 B2 | 1/2015 | Jacobsen |
| 8,956,310 B2 * | 2/2015 | Miyata .................. A61M 25/09 600/585 |
| 9,067,332 B2 | 6/2015 | Lippert |
| 9,067,333 B2 | 6/2015 | Lippert |
| 9,072,873 B2 | 7/2015 | Lippert |
| 9,072,874 B2 * | 7/2015 | Northrop ............ A61M 25/001 |
| 9,364,589 B2 | 6/2016 | Cage |
| 9,550,013 B2 * | 1/2017 | Kawasaki ............ A61L 31/022 |
| 9,616,195 B2 | 4/2017 | Lippert et al. |
| 9,623,212 B2 | 4/2017 | Tano |
| 9,662,798 B2 | 5/2017 | Christian |
| 9,700,702 B2 | 7/2017 | Tano |
| 9,848,882 B2 | 12/2017 | Lippert |
| 9,950,137 B2 | 4/2018 | Lippert et al. |
| 10,252,024 B2 | 4/2019 | Northrop |
| 10,363,389 B2 | 7/2019 | Lippert et al. |
| 10,639,456 B2 | 5/2020 | Peralta |
| 2001/0009980 A1 | 7/2001 | Richardson et al. |
| 2002/0013540 A1 * | 1/2002 | Jacobsen .............. A61M 25/09 600/585 |
| 2002/0019599 A1 * | 2/2002 | Rooney .................. A61M 25/09 600/585 |
| 2002/0049392 A1 | 4/2002 | DeMello |
| 2002/0062524 A1 | 5/2002 | Vogland et al. |
| 2002/0078808 A1 | 6/2002 | Jacobsen et al. |
| 2002/0082524 A1 | 6/2002 | Anderson |
| 2003/0009208 A1 | 1/2003 | Snyder et al. |
| 2003/0023190 A1 | 1/2003 | Cox |
| 2003/0069522 A1 | 4/2003 | Jacobsen |
| 2003/0093059 A1 * | 5/2003 | Griffin ............... A61M 25/0045 604/525 |
| 2004/0054349 A1 | 3/2004 | Brightbill |
| 2004/0087933 A1 | 5/2004 | Lee |
| 2004/0093060 A1 | 5/2004 | Seguin et al. |
| 2004/0102719 A1 * | 5/2004 | Keith .................. A61M 25/01 600/585 |
| 2004/0111044 A1 | 6/2004 | Davis |
| 2004/0167440 A1 * | 8/2004 | Sharrow ............ A61M 25/0108 600/585 |
| 2004/0181174 A2 * | 9/2004 | Davis ................ A61M 25/0013 600/585 |
| 2004/0186485 A1 | 9/2004 | Kear |
| 2004/0193140 A1 | 9/2004 | Griffin |
| 2004/0254450 A1 | 12/2004 | Griffin et al. |
| 2005/0054953 A1 * | 3/2005 | Ryan .................. A61M 25/09 600/585 |
| 2005/0124976 A1 | 6/2005 | Devens |
| 2005/0216049 A1 | 9/2005 | Jones et al. |
| 2005/0274384 A1 | 12/2005 | Tran et al. |
| 2006/0041186 A1 | 2/2006 | Vancaillie |
| 2006/0074442 A1 | 4/2006 | Noriega |
| 2006/0089618 A1 | 4/2006 | McFerran |
| 2006/0112802 A1 | 6/2006 | Fujinami |
| 2006/0121218 A1 * | 6/2006 | Obara .................. A61L 29/085 428/34.7 |
| 2006/0189896 A1 | 8/2006 | Davis et al. |
| 2006/0241519 A1 | 10/2006 | Hojeibane et al. |
| 2006/0262474 A1 | 11/2006 | Chen et al. |
| 2007/0010786 A1 | 1/2007 | Casey et al. |
| 2007/0100285 A1 | 5/2007 | Griffin |
| 2007/0112331 A1 * | 5/2007 | Weber .................. A61L 29/041 604/530 |
| 2007/0135763 A1 * | 6/2007 | Musbach .......... A61M 25/0054 604/96.01 |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0221230 A1 | 9/2007 | Thompson |
| 2007/0233039 A1 | 10/2007 | Mitelberg |
| 2007/0250036 A1 | 10/2007 | Volk |
| 2007/0287955 A1 | 12/2007 | Layman et al. |
| 2008/0021347 A1 | 1/2008 | Jacobsen et al. |
| 2008/0021401 A1 | 1/2008 | Jacobsen et al. |
| 2008/0021404 A1 | 1/2008 | Jacobsen et al. |
| 2008/0064989 A1 * | 3/2008 | Chen .................. A61M 25/09 600/585 |
| 2008/0077049 A1 | 3/2008 | Hirshman |
| 2008/0086854 A1 | 4/2008 | Boyd |
| 2008/0097246 A1 | 4/2008 | Stafford |
| 2008/0097247 A1 | 4/2008 | Eskuri |
| 2008/0097248 A1 * | 4/2008 | Munoz ............... A61M 25/0009 600/585 |
| 2008/0119869 A1 | 5/2008 | Teague et al. |
| 2008/0122226 A1 | 5/2008 | Madison |
| 2008/0125674 A1 | 5/2008 | Bilecen et al. |
| 2008/0147170 A1 * | 6/2008 | Vrba .................. A61M 25/00 623/1.22 |
| 2008/0188928 A1 | 8/2008 | Salahieh |
| 2008/0200839 A1 * | 8/2008 | Bunch .................. A61M 25/09 600/585 |
| 2008/0262474 A1 | 10/2008 | Northrop |
| 2008/0269641 A1 * | 10/2008 | O'Shaughnessy ........ A61F 2/86 600/585 |
| 2008/0319525 A1 | 12/2008 | Tieu |
| 2009/0036833 A1 | 2/2009 | Parins |
| 2009/0043283 A1 | 2/2009 | Turnlund |
| 2009/0043372 A1 | 2/2009 | Northrop et al. |
| 2009/0118675 A1 | 5/2009 | Czyscon et al. |
| 2009/0177119 A1 * | 7/2009 | Heidner ............... A61M 25/09 600/585 |
| 2009/0254000 A1 | 10/2009 | Layman et al. |
| 2009/0292225 A1 | 11/2009 | Chen et al. |
| 2009/0318892 A1 | 12/2009 | Aboytes et al. |

(56) References Cited

U.S. PATENT DOCUMENTS

| | | | |
|---|---|---|---|
| 2010/0063479 A1* | 3/2010 | Merdan | A61B 1/0011 604/528 |
| 2010/0114017 A1 | 5/2010 | Lenker et al. | |
| 2010/0114302 A1 | 5/2010 | Tzafriri et al. | |
| 2010/0139465 A1 | 6/2010 | Christian et al. | |
| 2010/0228150 A1 | 9/2010 | Zimmerman | |
| 2010/0256527 A1 | 10/2010 | Lippert et al. | |
| 2010/0256528 A1 | 10/2010 | Lippert | |
| 2010/0256601 A1 | 10/2010 | Lippert | |
| 2010/0256602 A1 | 10/2010 | Lippert | |
| 2010/0256603 A1 | 10/2010 | Lippert | |
| 2010/0256604 A1 | 10/2010 | Lippert | |
| 2010/0256605 A1 | 10/2010 | Lippert et al. | |
| 2010/0256606 A1 | 10/2010 | Lippert et al. | |
| 2010/0318066 A1 | 12/2010 | Miyata et al. | |
| 2011/0011226 A1 | 1/2011 | Tsurusawa | |
| 2011/0022003 A1 | 1/2011 | Tekulve | |
| 2011/0160680 A1 | 6/2011 | Cage et al. | |
| 2012/0065623 A1 | 3/2012 | Nelson, III | |
| 2012/0158034 A1 | 6/2012 | Wilson | |
| 2012/0209073 A1* | 8/2012 | McWeeney | A61B 1/00071 600/146 |
| 2012/0239074 A1 | 9/2012 | Aboytes et al. | |
| 2012/0271397 A1 | 10/2012 | Muzslay et al. | |
| 2013/0018359 A1 | 1/2013 | Coyle | |
| 2013/0096553 A1 | 4/2013 | Hill et al. | |
| 2013/0110000 A1 | 5/2013 | Tully | |
| 2013/0226033 A1 | 8/2013 | Eskuri | |
| 2013/0255456 A1 | 10/2013 | Christian | |
| 2014/0094787 A1 | 4/2014 | Reynolds | |
| 2014/0187983 A1 | 7/2014 | Anderson | |
| 2014/0257363 A1 | 9/2014 | Lippert | |
| 2014/0276109 A1 | 9/2014 | Gregorich | |
| 2014/0276787 A1 | 9/2014 | Wang et al. | |
| 2014/0336620 A1 | 11/2014 | Layman et al. | |
| 2015/0011964 A1 | 1/2015 | Abner | |
| 2015/0190614 A1 | 7/2015 | Uihlein | |
| 2015/0238734 A1 | 8/2015 | Kanazawa | |
| 2015/0290432 A1 | 10/2015 | Matthews | |
| 2015/0297863 A1 | 10/2015 | Hannon et al. | |
| 2015/0305710 A1 | 10/2015 | Koninklijke | |
| 2015/0306355 A1 | 10/2015 | Idstrom | |
| 2016/0008585 A1 | 1/2016 | Tano | |
| 2016/0045101 A1 | 2/2016 | Nakatate et al. | |
| 2016/0089128 A1 | 3/2016 | Weber et al. | |
| 2016/0113793 A1 | 4/2016 | Nishigishi | |
| 2016/0135827 A1 | 5/2016 | Elsesser | |
| 2016/0199620 A1 | 7/2016 | Pokorney | |
| 2016/0235337 A1 | 8/2016 | Govari | |
| 2016/0361520 A1 | 12/2016 | Braun | |
| 2016/0367788 A1 | 12/2016 | Jimenez et al. | |
| 2016/0375226 A1 | 12/2016 | Nabeshima | |
| 2017/0189643 A1 | 7/2017 | Christian | |
| 2017/0281909 A1 | 10/2017 | Northrop et al. | |
| 2018/0015261 A1 | 1/2018 | Lippert | |
| 2018/0015263 A1 | 1/2018 | Lippert | |
| 2018/0028177 A1 | 2/2018 | Van et al. | |
| 2018/0071496 A1 | 3/2018 | Snyder | |
| 2018/0177517 A1 | 6/2018 | Lippert | |
| 2018/0185619 A1* | 7/2018 | Batman | A61M 25/09 |
| 2018/0193607 A1 | 7/2018 | Lippert et al. | |
| 2019/0105463 A1 | 4/2019 | Christian et al. | |
| 2019/0255290 A1 | 8/2019 | Snyder et al. | |
| 2020/0345975 A1 | 11/2020 | Snyder | |

FOREIGN PATENT DOCUMENTS

| | | |
|---|---|---|
| AU | 774559 | 7/2004 |
| AU | 2008229892 | 10/2008 |
| BR | 9709363 | 1/2000 |
| BR | 9712829 | 1/2000 |
| CA | 2266685 | 5/2006 |
| CA | 2255781 | 3/2007 |
| CA | 2395149 | 12/2008 |
| CN | 1230914 | 10/1999 |
| CN | 1324285 | 11/2001 |
| CN | 1422673 | 6/2003 |
| CN | 1518428 | 8/2004 |
| CN | 1781684 | 6/2006 |
| CN | 101001660 | 7/2007 |
| CN | 101209365 A | 7/2008 |
| CN | 101304778 | 11/2008 |
| CN | 102049085 A | 5/2011 |
| CN | 102107041 A | 6/2011 |
| CN | 102824681 A | 12/2012 |
| CN | 104271035 A | 1/2015 |
| CN | 105209102 A | 12/2015 |
| DE | 60036882 | 7/2008 |
| DE | 69738235 | 7/2008 |
| EP | 0998323 A1 | 5/2000 |
| EP | 0934141 | 11/2005 |
| EP | 0921754 | 10/2007 |
| EP | 1239901 | 10/2007 |
| EP | 1940498 | 7/2008 |
| EP | 2964305 | 1/2016 |
| ES | 2293660 | 3/2008 |
| JP | 59102509 | 6/1984 |
| JP | 07-008560 | 1/1995 |
| JP | 08-308934 | 11/1996 |
| JP | 11294497 | 10/1999 |
| JP | 2000116787 | 4/2000 |
| JP | 2000511094 | 8/2000 |
| JP | 2000343313 | 12/2000 |
| JP | 2001500808 | 1/2001 |
| JP | 2002543896 | 12/2002 |
| JP | 2003011117 | 1/2003 |
| JP | 2004-136121 A | 5/2004 |
| JP | 200425340 | 5/2004 |
| JP | 2004329552 | 11/2004 |
| JP | 2004535233 | 11/2004 |
| JP | 2005533594 | 11/2005 |
| JP | 2007313638 | 12/2007 |
| JP | 2008536639 | 9/2008 |
| JP | 2010535588 | 11/2010 |
| JP | 4805208 | 11/2011 |
| JP | 4845313 | 12/2011 |
| KR | 20000015896 | 3/2000 |
| KR | 20000036139 | 6/2000 |
| TW | 412468 | 11/2000 |
| WO | 9419039 | 1/1994 |
| WO | 1994006503 | 3/1994 |
| WO | 99/04847 A1 | 2/1999 |
| WO | 9953824 | 10/1999 |
| WO | 2004011076 | 2/2004 |
| WO | 2006/025931 A1 | 3/2006 |
| WO | 2006113863 | 10/2006 |
| WO | 2007050718 | 5/2007 |
| WO | 2009/020691 A2 | 2/2009 |
| WO | 2009020961 | 2/2009 |
| WO | 2009020962 | 2/2009 |
| WO | 2010077692 | 7/2010 |
| WO | 2010115163 | 10/2010 |
| WO | 2014066104 | 5/2014 |
| WO | 2014138580 | 9/2014 |
| WO | 2016047499 | 3/2016 |
| WO | 2016117238 | 7/2016 |
| WO | 2016136609 | 9/2016 |
| WO | 2016152194 | 9/2016 |
| WO | 2016158671 | 10/2016 |
| WO | 2018218216 | 11/2018 |

OTHER PUBLICATIONS

European Search Report for application No. 17184064.8 dated Jan. 5, 2018.
U.S. Appl. No. 12/753,858, filed Oct. 20, 2017, Final Office Action.
International Search Report and Written Opinion for application No. PCT/US17/41299 dated Oct. 2, 2017.
International Search Report and Written Opinion for application No. PCT/US17/41301 dated Oct. 2, 2017.
International Search Report and Written Opinion for application No. PCT/US17/41305 dated Oct. 2, 2017.

(56) References Cited

OTHER PUBLICATIONS

U.S. Appl. No. 12/753,836, dated Nov. 24, 2017, Notice of Allowance.
Supplementary Partial European Search Report for EP14760849 dated Oct. 11, 2016.
International Search Report and Written Opinion for PCT/US2014/021742 dated Aug. 27, 2014.
International Search Report and Written Opinion for application PCT/US2017/050802 dated Nov. 7, 2017.
International Search Report and Written Opinion for PCT/US2017/068056 dated Feb. 26, 2018.
International Search Report and Written Opinion for PCT/US2018/034723 dated Sep. 5, 2018.
International Search Report and Written Opinion for PCT/US2018/034756 dated Aug. 14, 2018.
U.S. Appl. No. 14/199,675, Nov. 3, 2016, Office Action.
U.S. Appl. No. 14/199,675, May 18, 2017, Final Office Action.
U.S. Appl. No. 14/199,675, Sep. 6, 2017, Notice of Allowance.
U.S. Appl. No. 12/753,858, Nov. 14, 2018, Final Office Action.
U.S. Appl. No. 15/917,255, Mar. 9, 2018, Lippert.
U.S. Appl. No. 12/753,858, Mar. 13, 2018, Office Action.
U.S. Appl. No. 15/465,399, Apr. 23, 2018, Office Action.
U.S. Appl. No. 15/465,399, Sep. 10, 2018, Notice of Allowance.
EP10759515.9 Supplementary European Search Report dated Sep. 25, 2012.
International Search Report for PCT/US2009/067217 dated Dec. 16, 2010.
International Search Report for PCT/US2010/029867 dated Jun. 1, 2010.
European Search Report for EP09836735 dated Nov. 7, 2012.
European Search Report for EP15197042 dated Apr. 11, 2016.
U.S. Appl. No. 12/753,836, Jul. 14, 2017, Final Office Action.
U.S. Appl. No. 12/753,831, Feb. 1, 2012, Office Action.
U.S. Appl. No. 12/753,831, May 31, 2012, Final Office Action.
U.S. Appl. No. 12/753,836, Dec. 9, 2011, Office Action.
U.S. Appl. No. 12/753,836, May 1, 2012, Final Office Action.
U.S. Appl. No. 12/753,839, Feb. 7, 2012, Office Action.
U.S. Appl. No. 12/753,839, May 31, 2012, Final Office Action.
U.S. Appl. No. 12/753,842, Aug. 1, 2012, Office Action.
U.S. Appl. No. 12/753,855, Sep. 15, 2011, Office Action.
U.S. Appl. No. 12/753,855, Apr. 18, 2012, Final Office Action.
U.S. Appl. No. 12/753,858, May 10, 2011, Office Action.
U.S. Appl. No. 12/753,858, Oct. 19, 2011, Final Office Action.
U.S. Appl. No. 12/753,858, Feb. 3, 2012, Office Action.
U.S. Appl. No. 12/753,858, Jul. 18, 2012, Final Office Action.
U.S. Appl. No. 12/753,849, May 10, 2011, Office Action.
U.S. Appl. No. 12/753,849, Oct. 18, 2011, Office Action.
U.S. Appl. No. 12/753,849, Jun. 6, 2012, Final Office Action.
U.S. Appl. No. 12/633,727, Oct. 16, 2012, Office Action.
U.S. Appl. No. 12/633,727, Feb. 28, 2013, Notice of Allowance.
U.S. Appl. No. 12/753,849, Oct. 9, 2013, Final Office Action.
U.S. Appl. No. 12/753,858, Jan. 17, 2014, Final Office Action.
U.S. Appl. No. 12/753,842, Jan. 29, 2014, Office Action.
U.S. Appl. No. 12/753,855, Feb. 28, 2014, Office Action.
U.S. Appl. No. 12/753,831, Mar. 21, 2014, Office Action.
U.S. Appl. No. 12/753,849, May 27, 2014, Office Action.
U.S. Appl. No. 12/753,836, Jul. 31, 2014, Office Action.
U.S. Appl. No. 12/753,831, Aug. 29, 2014, Final Office Action.
U.S. Appl. No. 12/753,839, May 5, 2014, Office Action.
U.S. Appl. No. 12/753,842, Jan. 9, 2013, Final Office Action.
U.S. Appl. No. 12/753,849, Jan. 3, 2013, Office Action.
U.S. Appl. No. 12/753,858, Mar. 29, 2013, Office Action.
U.S. Appl. No. 12/753,842, Sep. 4, 2014, Final Office Action.
U.S. Appl. No. 12/753,858, Sep. 4, 2014, Office Action.
U.S. Appl. No. 12/753,858, Nov. 4, 2014, Interview Summary.
U.S. Appl. No. 12/753,836, Jan. 9, 2015, Final Office Action.
U.S. Appl. No. 12/753,849, Dec. 5, 2014, Interview Summary.
U.S. Appl. No. 12/753,842, Dec. 29, 2014, Notice of Allowance.
U.S. Appl. No. 12/753,855, Jan. 13, 2015, Final Office Action.
U.S. Appl. No. 12/753,849, Feb. 2, 2015, Notice of Allowance.
U.S. Appl. No. 12/753,842, Mar. 5, 2015, Notice of Allowance.
U.S. Appl. No. 12/753,831, Apr. 14, 2015, Notice of Allowance.
U.S. Appl. No. 12/753,849, Apr. 30, 2015, Notice of Allowance.
U.S. Appl. No. 12/753,855, May 21, 2015, Office Action.
U.S. Appl. No. 12/753,858, May 28, 2015, Final Office Action.
U.S. Appl. No. 12/753,836, Jun. 26, 2015, Office Action.
U.S. Appl. No. 13/901,375, Dec. 10, 2015, Office Action.
U.S. Appl. No. 12/753,858, Dec. 30, 2015, Office Action.
U.S. Appl. No. 12/753,836, Feb. 17, 2016, Final Office Action.
U.S. Appl. No. 12/753,855, May 5, 2016, Office Action.
U.S. Appl. No. 13/901,375, Aug. 1, 2016, Office Action.
U.S. Appl. No. 12/753,858, Oct. 24, 2016, Office Action.
U.S. Appl. No. 12/753,855, Nov. 30, 2016, Notice of Allowance.
U.S. Appl. No. 12/753,836, Dec. 23, 2016, Office Action.
U.S. Appl. No. 13/901,375, Dec. 27, 2016, Notice of Allowance.
U.S. Appl. No. 12/753,858, Mar. 27, 2017, Office Action.
U.S. Appl. No. 15/611,344, Mar. 26, 2019, Office Action.
U.S. Appl. No. 16/281,046, Feb. 20, 2019, Snyder.
U.S. Appl. No. 16/439,894, Jun. 13, 2019, Lippert.
International Search Report and Written Opinion for PCT/US2019/019046 dated May 17, 2019.
U.S. Appl. No. 15/606,607, May 14, 2019, Office Action.
U.S. Appl. No. 12/753,858, Mar. 14, 2019, Notice of Allowance.
U.S. Appl. No. 15/698,553, May 15, 2020, Notice of Allowance.
U.S. Appl. No. 15/611,344, May 21, 2020, Office Action.
U.S. Appl. No. 15/848,878, Oct. 29, 2019, Office Action.
U.S. Appl. No. 15/848,878, Feb. 5, 2020, Office Action.
U.S. Appl. No. 15/698,553, Nov. 27, 2019, Office Action.
U.S. Appl. No. 16/212,425, filed Dec. 6, 2018, Christian.
International Search Report and Written Opinion for PCT/US2019/021031 dated Jun. 18, 2019.
U.S. Appl. No. 15/611,344, Nov. 12, 2019, Final Office Action.
U.S. Appl. No. 15/606,607, Nov. 19, 2019, Final Office Action.
U.S. Appl. No. 16/212,425, Mar. 16, 2020, Office Action.
International Search Report and Written Opinion for Application PCT/US2017/050602 dated Nov. 7, 2017.
International Search Report and Written Opinion received for PCT Patent Application No. PCT/US2020/030589, dated Jul. 17, 2020, 7 pages.
International Search Report and Written Opinion, PCT App. No. PCT/US2020/013754, dated Jun. 9, 2020, 11 pages.
Non-Final Office Action received for U.S. Appl. No. 15/606,607, dated Jun. 10, 2020, 26 pages.
Office Action received for U.S. Appl. No. 15/698,553, dated Nov. 27, 2019.
Non-Final Office Action received for U.S. Appl. No. 16/281,046, dated Oct. 29, 2020, 18 pages.
Final Rejection received for U.S. Appl. No. 15/606,607, dated Dec. 15, 2020, 24 pages.

* cited by examiner

GUIDEWIRE DEVICES HAVING DISTALLY EXTENDING COILS AND SHAPEABLE TIPS

CROSS-REFERENCE TO RELATED APPLICATIONS

This application claims priority to and the benefit of U.S. Provisional Patent Application Ser. No. 62/363,760, filed Jul. 18, 2016 and titled "GUIDEWIRE DEVICES HAVING SHAPEABLE TIPS," the disclosure of which is incorporated herein by this reference in its entirety.

BACKGROUND

Guidewire devices are often used to lead or guide catheters or other interventional devices to a targeted anatomical location within a patient's body. Typically, guidewires are passed into and through a patient's vasculature in order to reach the target location, which may be at or near the patient's heart or neurovascular tissue, for example. Radiographic imaging is typically utilized to assist in navigating a guidewire to the targeted location. In many instances, a guidewire is left in place within the body during the interventional procedure where it can be used to guide multiple catheters or other interventional devices to the targeted anatomical location.

Some guidewire devices are constructed with a curved or bent tip to enable an operator to better navigate a patient's vasculature. With such guidewires, an operator can apply a torque to the proximal end of the guidewire or attached proximal handle in order to orient and point the tip in a desired direction. The operator may then direct the guidewire further within the patient's vasculature in the desired direction.

Tuning the flexibility of a guidewire device, particularly the distal sections of the guidewire device, is also a concern. In many circumstances, relatively high levels of flexibility are desirable in order to provide sufficient bendability of the guidewire to enable the guidewire to be angled through the tortuous bends and curves of a vasculature passageway to arrive at the targeted area. For example, directing a guidewire to portions of the neurovasculature requires passage of the guidewire through curved passages such as the carotid siphon and other tortuous paths.

Another concern related to guidewire devices is the ability of a given guidewire device to transmit torque from the proximal end to the distal end (i.e., the "torquability" of the guidewire device). As more of a guidewire is passed into and through a vasculature passageway, the amount of frictional surface contact between the guidewire and the vasculature increases, hindering easy movement of the guidewire through the vasculature passage. A guidewire with good torquability enables torqueing forces at the proximal end to be transmitted through the guidewire to the distal end so that the guidewire can rotate and overcome the frictional forces.

Some guidewire devices include a distally placed micromachined hypotube positioned over the distal end of the guidewire core in order to direct applied torsional forces further distally toward the end of the device. Because torsional forces are primarily transmitted through the outer sections of a cross-section of a member, the tube is configured to provide a path for increased transmission of torque as compared to the amount of torque transmitted by a guidewire core not sheathed by a tube.

While such guidewire devices have provided many benefits, several limitations remain. For example, many of the design characteristics of a guidewire having a torque-transmitting tube, although functioning to provide increased torque transmission, work against and limit the shapeability of the guidewire tip.

BRIEF SUMMARY

The present disclosure relates to guidewire devices having shapeable tips and effective torquability. In one embodiment, a guidewire device includes a core with a proximal section and a distal section. The distal section may taper to a smaller diameter than at the proximal section. A tube structure is coupled to the core such that the distal section of the core passes into the tube structure and passes distally beyond the tube structure to form a shapeable tip. The guidewire device also includes an inner coil that encompasses at least a portion of the distal portion of the core. The inner coil is positioned such that a proximal portion of the inner coil is disposed between an outer surface of the core and an inner surface of the tube structure, and such that a distal portion of the inner coil extends distally beyond the tube structure to encompass at least a portion of the shapeable tip. The guidewire device also includes an outer coil coupled to a distal end of the tube structure and extending distally from the tube structure. The outer coil is positioned to encompass at least a portion of the inner coil. The tip is configured to reduce the tendency of resilient forces from the tube structure to disrupt a customized shape of the tip.

In one embodiment, the core is formed from and/or includes stainless steel, the tube structure is formed from and/or includes a superelastic material such as nitinol, the inner coil is formed from and/or includes a radiopaque material such as platinum, and the outer coil is formed from and/or includes stainless steel.

In some embodiments, the tube structure includes a plurality of fenestrations that define a plurality of axially extending beams coupling a plurality of circumferentially extending rings. The tube structure may include one or more of a one-beam, two-beam, three-beam cut pattern, or cut pattern of more than three beams. In some embodiments, a rotational offset is applied between successive segments to minimize preferred bending directions along a length of the tube structure.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Introduction

The present disclosure relates to guidewire devices providing effective anatomical navigation capabilities. The ability to steer and direct a guidewire to a targeted anatomical location depends on balancing and optimizing tradeoffs between torquability and the ability to maintain a shaped tip. A guidewire device may include a shapeable tip to allow an operator to point the tip in a desired direction within the vasculature by rotating the distal tip. However, if the torquability of such a guidewire device is insufficient, the operator will be unable to transmit torsional forces all the way to the shaped distal tip to control the orientation of the shaped distal tip. This hindrance will become increasingly problematic as the guidewire device is advanced farther into the vasculature and experiences increasing frictional resistance. In addition, if a guidewire device is unable to properly form and maintain a shaped tip, it will have limited ability to adjust tip orientation, making intravascular navigation more difficult.

Embodiments described herein provide one or more features that balance and/or optimize the relationship between guidewire torquability and the ability to form and maintain a shaped tip. Such guidewires are responsive to operator manipulation during guidewire deployment, and provide effective navigation capabilities by enabling a shaped distal tip to receive transmitted torsional forces.

In some embodiments, the shapeable tip allows an operator to custom shape the tip, such as by manually shaping the tip just prior to deploying the guidewire device within the patient's vasculature. The operator is thus enabled to customize the shaping of the distal tip according to preferences and/or conditions particular to a given application. The guidewire device is also configured to effectively transmit torque while maintaining the shaped tip. At least some embodiments described herein include tips that are able to maintain a bent or curved shape throughout a procedure, or throughout multiple procedures, or even indefinitely until subjected to a counteracting reshaping force.

Guidewire Devices with Shapeable Tips

Figure 1:
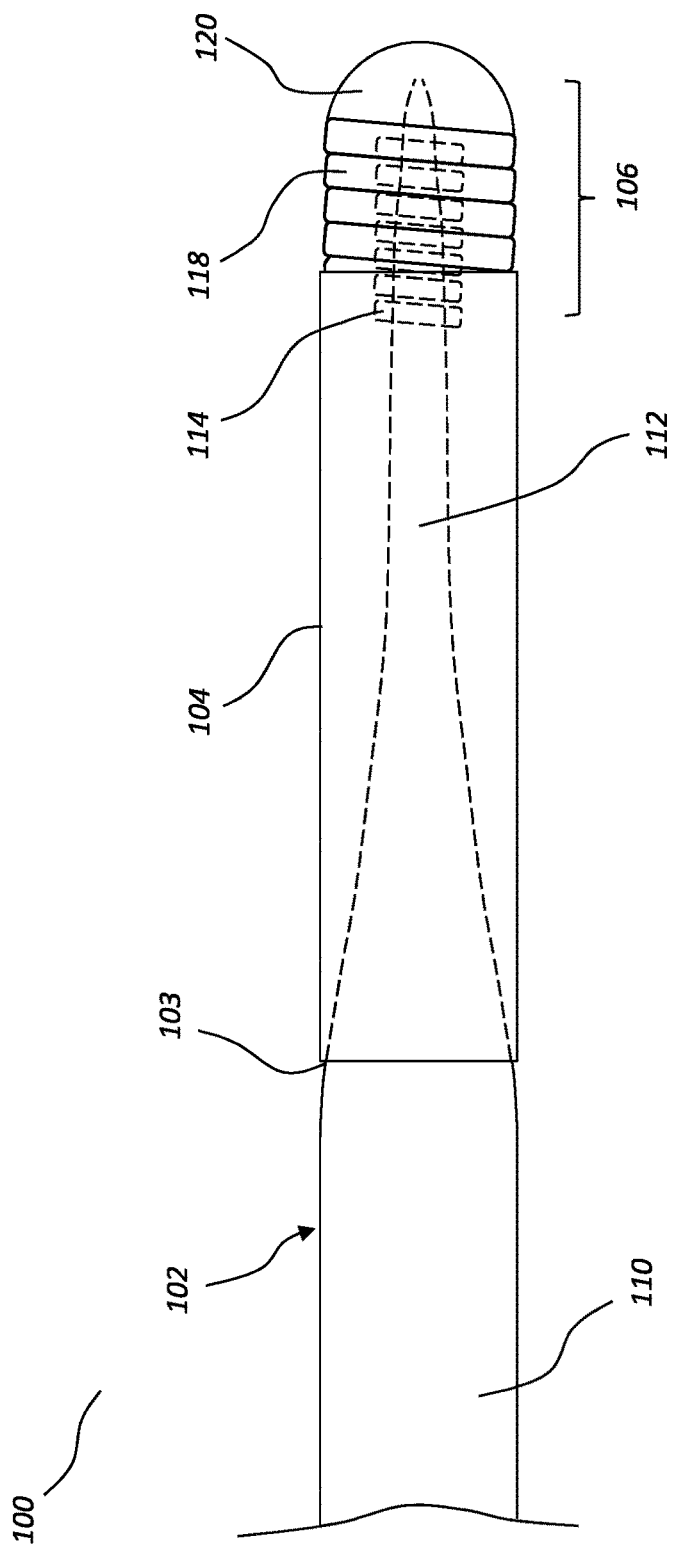
FIG. 1 illustrates an exemplary embodiment of a guidewire device providing effective torquability and having a shapeable tip.
Figure 2:
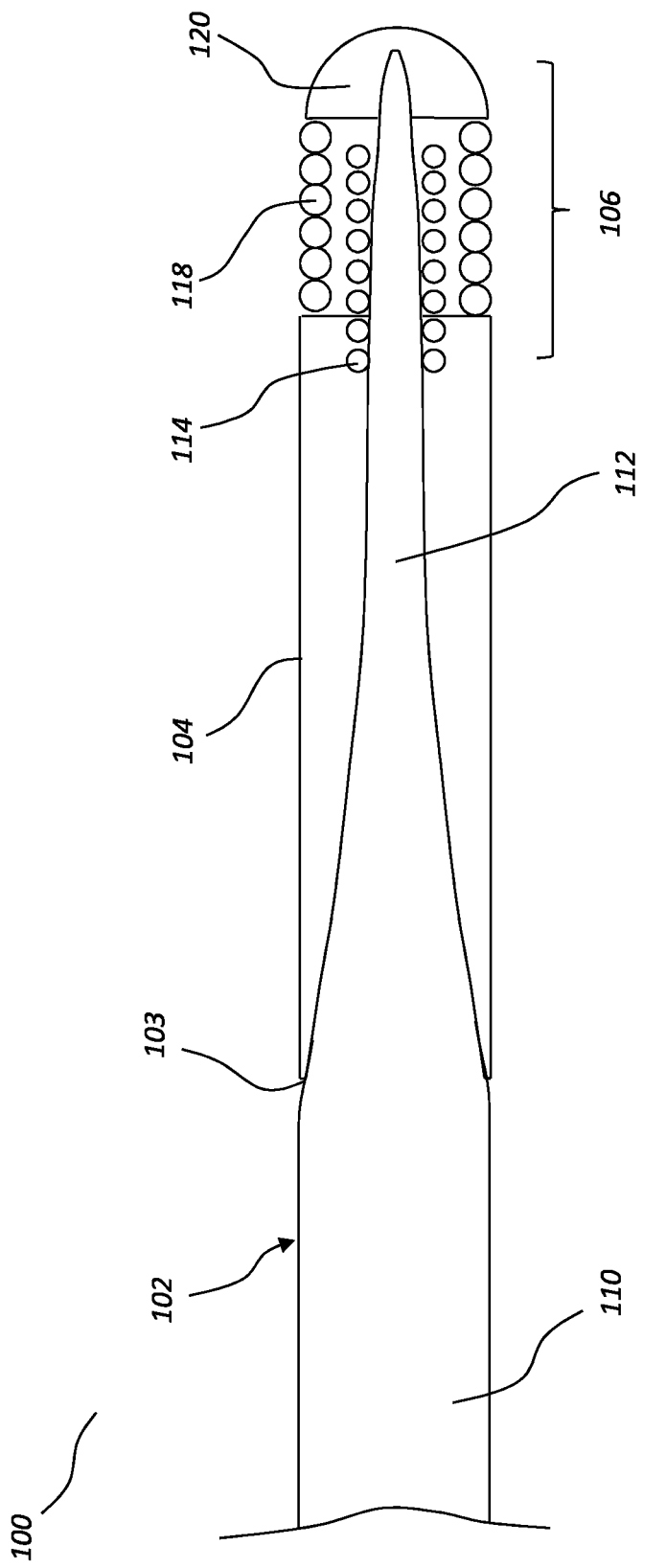
FIG. 2 is a cross-sectional view of the guidewire device of FIG. 1.

FIGS. 1 and 2 illustrate an exemplary guidewire device 100 having an effective shapeable tip. FIG. 1 illustrates a side view of the device and FIG. 2 illustrates a cross-sectional view of the device. The guidewire device 100 includes a core 102. A tube 104 is coupled to the core 102 and extends distally from a point of attachment to the core 102. As shown, a distal section of the core 102 extends into the tube 104 and is surrounded by the tube 104. In some embodiments, the core 102 includes one or more tapering sections so that the core 102 is able to fit within and extend into the tube 104. For example, the distal section of the core 102 may be ground so as to progressively taper to a smaller diameter at the distal end. In this example, the core 102 and the tube 104 have substantially similar outer diameters at the attachment point 103 where they adjoin and attach to one another.

The tube 104 is coupled to the core 102 (e.g., using adhesive, soldering, and/or welding) in a manner that allows torsional forces to be transmitted from the core 102 to the tube 104 and thereby to be further transmitted distally by the tube 104. A medical grade adhesive may be used to couple the tube 104 to the core wire 102 at one or more points (e.g., including attachment point 103). A medical grade adhesive/polymer may also be used at the distal end of the device and to form an atraumatic covering 120.

As explained in more detail below, the tube 104 is micro-fabricated to include a plurality of cuts. The cuts are arranged to form a cut pattern which beneficially provides for effective shapeability near the distal tip of the guidewire device 100 while also maintaining good torquability. For clarity, the cut pattern is not shown in FIGS. 1 and 2. Examples of cut patterns which may be utilized in the tube 104 are shown in FIGS. 3 through 8.

In some embodiments, the proximal section 110 of the guidewire device 100 extends proximally to a length necessary to provide sufficient guidewire length for delivery to a targeted anatomical area (not shown). The proximal section 110 typically has a length ranging from about 50 to 300 cm (about 19.69 to 118.11 inches). The proximal section 110 may have a diameter of about 0.36 mm (about 0.014 inches), or a diameter within a range of about 0.20 to 3.175 mm (about 0.008 to 0.125 inches). The distal section 112 of the core 102 may taper to a diameter of about 0.051 mm (about 0.002 inches), or a diameter within a range of about 0.025 to 1.27 mm (about 0.001 to 0.050 inches). In some embodiments, the tube 104 has a length within a range of about 3 to 100 cm (about 1.18 to 39.37 inches). The tube 104 may be formed from and/or include a superelastic material such as nitinol. Alternatively, the tube 104 may be formed from and/or include a linear elastic material (e.g., with a recoverable strain of at least about 6%). The portion of the device extending distally beyond the tube 104 (referred to as the tip 106) may measure about 0.5 to 5 cm in length, or about 1 to 3 cm in length.

In some embodiments, the distal section 112 of the core 102 tapers to a round cross-section. In other embodiments, the distal section 112 of the core 102 has a flat or rectangular cross-section. The distal section 112 may also have another cross-sectional shape, such as another polygon shape, an ovoid shape, an erratic shape, or combination of different cross-sectional shapes at different areas along its length.

Typically, a user will shape the distal end of the guidewire device 100 by manually bending, twisting, or otherwise manipulating the distal 1 cm to 3 cm (approximately) of the guidewire device 100 to a desired shape. The illustrated guidewire device 100 includes a distal tip 106 which extends distally beyond the tube 104. The tip 106 is configured to be shapeable so that an operator may manually bend, twist, or otherwise manipulate the tip 106 to a desired shape. In some embodiments, the tip 106 includes one or more shapeable components formed from stainless steel, platinum, and/or other shapeable materials. In preferred embodiments, the tip 106 includes one or more components formed from a material that exhibits work hardening properties, such that the tip, when shaped (i.e., plastically deformed), provides a higher elastic modulus at the shaped sections than prior to being shaped.

An inner coil 114 is positioned partially within the tube 104 upon at least a portion of the distal section 112 of the core 102. The inner coil 114 extends distally beyond the tube 104 to form part of the tip 106. The inner coil 114 is preferably formed from one or more radiopaque materials, such as platinum group, gold, silver, palladium, iridium, osmium, tantalum, tungsten, bismuth, dysprosium, gadolinium, and the like. Additionally, or alternatively, the coil 114 may be at least partially formed from a stainless steel or other material capable of effectively holding shape after being bent or otherwise manipulated by a user.

In the illustrated embodiment, the inner coil 114 is disposed at or near the distal end of the device and extends a distance proximally toward the attachment point 103. In the illustrated device, the majority of the length of the inner coil 114 extends distally beyond the tube 104. In other embodiments, the inner coil 114 may extend farther proximally. The inner coil 114 may extend from the distal end by 1, 2, 4, 6, 8, 10, 12, 15, 20, 25, 30, or 35 cm, or may extend a distance within a range defined by any two of the foregoing values.

In some embodiments, the section of the inner coil 114 extending distally beyond the tube 104 may be formed from a different material than more proximal sections of the inner coil 114. For example, the distal section of the inner coil 114 may be formed from stainless steel and/or other materials primarily selected to provide effective shapeability, while the proximal sections of the inner coil 114 are formed from platinum or other materials primarily selected to provide effective radiopacity. In some embodiments, the inner coil 114 is formed as one integral piece. In other embodiments, the inner coil 114 includes a plurality of separate sections positioned adjacent to one another and/or interlocked through intertwining coils. Such separate segments may additionally or alternatively be soldered, adhered, or otherwise fastened to one another to form the complete inner coil 114.

Although the illustrated embodiment shows a space between the outer surface of the inner coil 114 and the inner surface of the tube 104, it will be understood that this is done schematically for ease of visualization. In some embodiments, the inner coil 114 is sized to fill and pack a greater proportion of the space between the core 102 and the tube 104. For example, the inner coil 114 may be sized so as to abut both the outer surface of the core 102 and the inner surface of the tube 104. Some embodiments may include a space between the core 102 and the tube 104 for at least a portion of the section of the guidewire device 100 where the tube 104 and the core 102 are co-extensive.

The portion of the inner coil 114 disposed within the tube 104 may beneficially function to pack the space between the core 102 and the tube 104 so as to align the curvature of the distal section 112 of the core 102 with the curvature of the tube 104. For example, when a curvature is formed in the tube 104, the closely packed segments of the inner coil 114 function as a packing between the tube 104 and the distal section 112 to impart the same curvature to the distal section 112. In contrast, a core of a guidewire device omitting such packing, may not follow the same curve as the tube but may extend until abutting against the inner surface of the tube before being forced to curve.

As shown, the tip 106 extends further distally than the tube 104. The illustrated configuration beneficially allows the tip 106 to be shaped to a desired position relative to the tube 104 and the rest of the guidewire 100 and to remain in the shaped position for a sufficiently extended period of time. In contrast to a guidewire device relying on shapeability of a tube or upon shapeable components disposed more fully within a tube, the illustrated tip 106 is able to maintain a shaped configuration without being subjected to counteracting forces imparted by the tube 104 itself.

In addition, as described more fully below, the tube 104 may include a cut pattern which maintains effective torquability while also providing sufficient flexibility at the distal region of the tube 104 so as to avoid disrupting the custom shape of the tip 106. In preferred embodiments, the shapeable distal section of the core has a stiffness that is able to withstand an expected bending force from the tube acting upon the distal section of the core after it has been shaped. In some embodiments, the shapeable distal section of the core is formed from a material or combination of materials providing a modulus of elasticity that is about 1.5 to 4 times greater, or about 2 to 3 times greater than the modulus of elasticity of the material(s) used to form the tube.

In contrast to the illustrated embodiments, a guidewire device which relies on shaping of a tube to provide a desired distal tip shape will not be capable of holding the shaped configuration or will only be capable of holding the shaped configuration for a relatively short period of time. This degradative effect on the shaped tip happens at least in part because tube structures are typically formed from nitinol or other superelastic materials. Such tubes will be biased, upon being bent or shaped, toward their original (e.g., straight) position, and will impart recovery forces against any shapeable internal components, resulting in deformation and a loss of the customized shape of the tip.

Often, for example, a guidewire that distally terminates with a tube structure or that otherwise substantially relies on bending of the tube structure to shape the tip will have a shaped tip prior to deployment. However, the shaped tip will be lost or degraded during use of the guidewire as the superelastic tube flexes toward its original shape in opposition to the desired tip shape. In contrast, embodiments described herein provide tips capable of being shaped without being subjected to deforming recovery forces of adjoining components of the guidewire device.

In the illustrated guidewire device 100, an outer coil 118 overlies the distally extending section of the inner coil 114. The inner coil 114 and outer coil 118 may use similar or dissimilar coil characteristics (coil wire diameter, pitch, etc.). Typically, the outer coil 118 is formed from larger diameter coil wiring as compared to the wire diameter of the inner coil 114. The outer coil 118 may be formed from stainless steel or other suitable material capable of providing suitable shapeability.

Cut Patterns

FIGS. 3 through 8 illustrate exemplary embodiments of tube cut patterns that may be utilized in one or more of the guidewire device embodiments described herein. For example, the tube 104 of the embodiment shown in FIGS. 1 and 2 may be cut according to one or more of the configurations shown in FIGS. 3 through 8.

Figure 3:
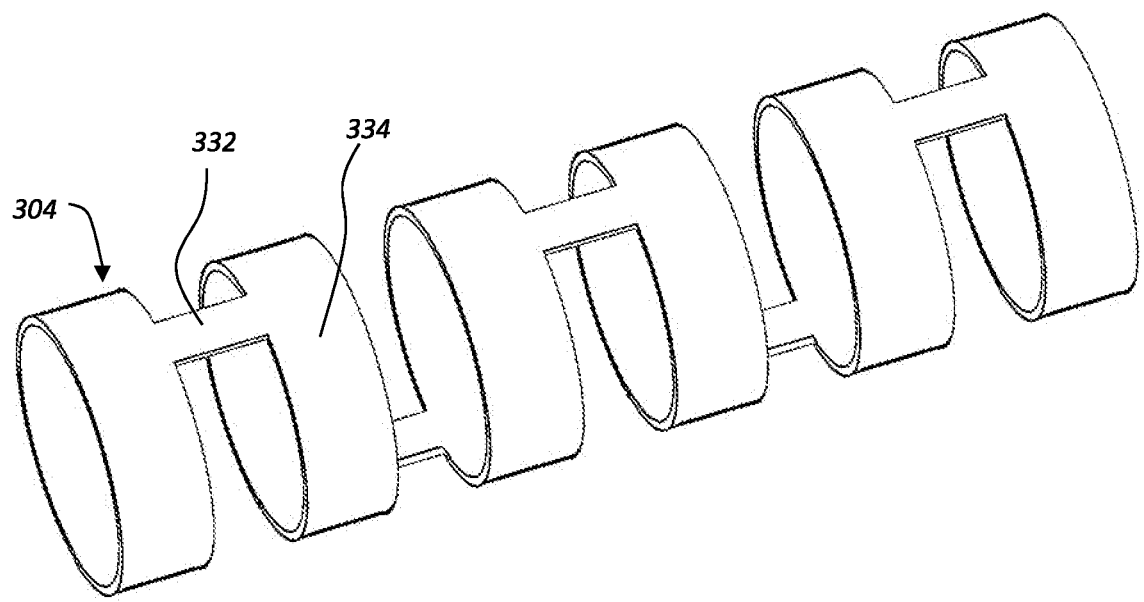
FIGS. 3 through 8 illustrate various exemplary cut patterns that may be formed in the tube of the guidewire device.
Figure 4:
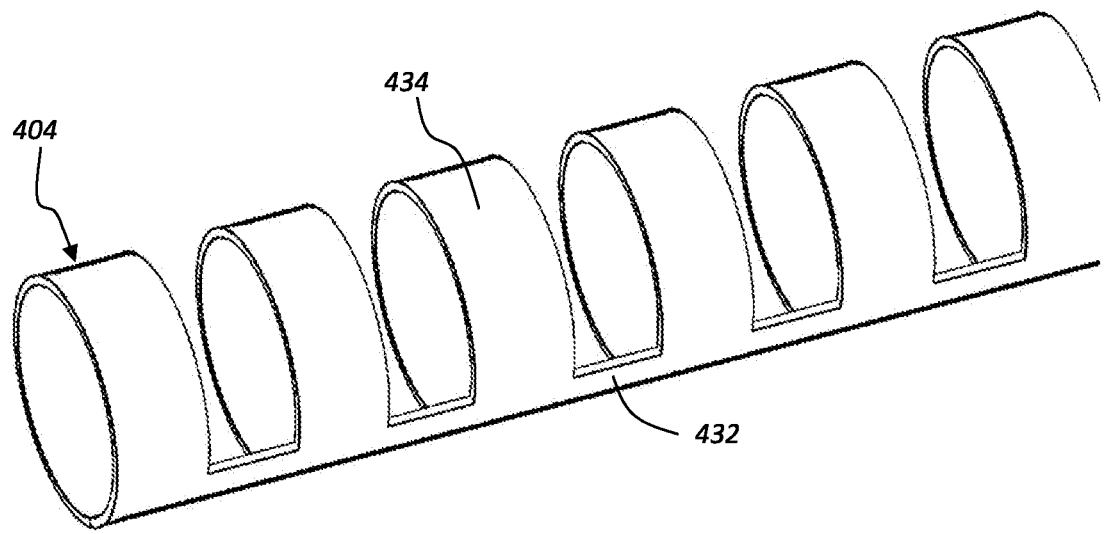
Figure 5:
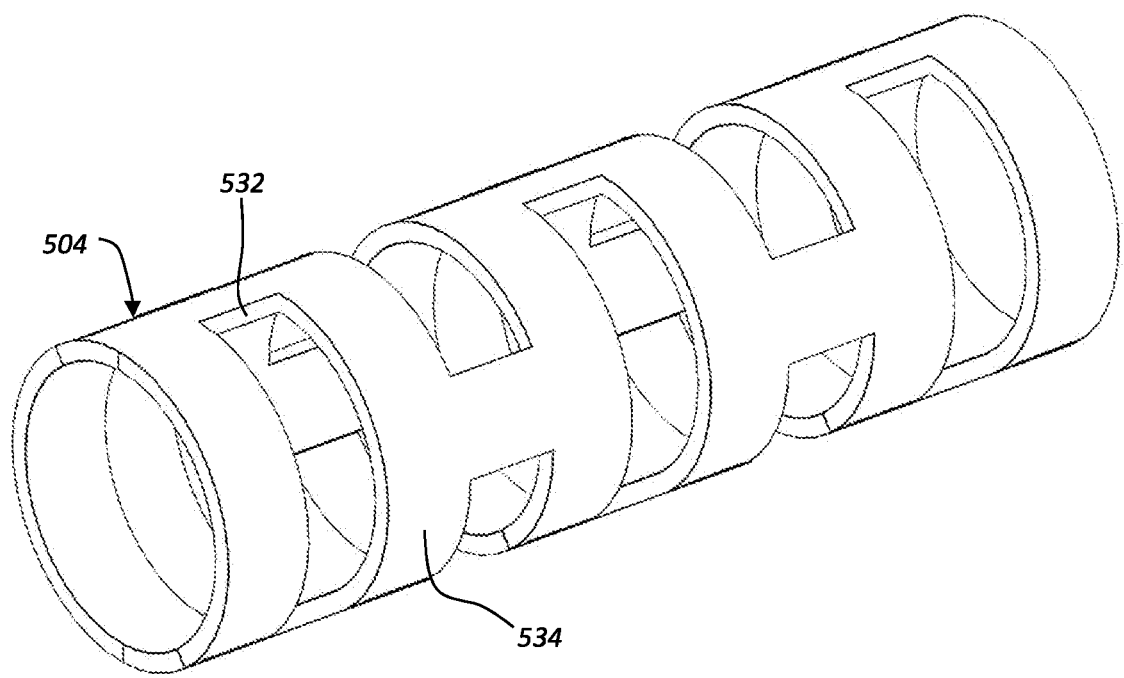
Figure 6:
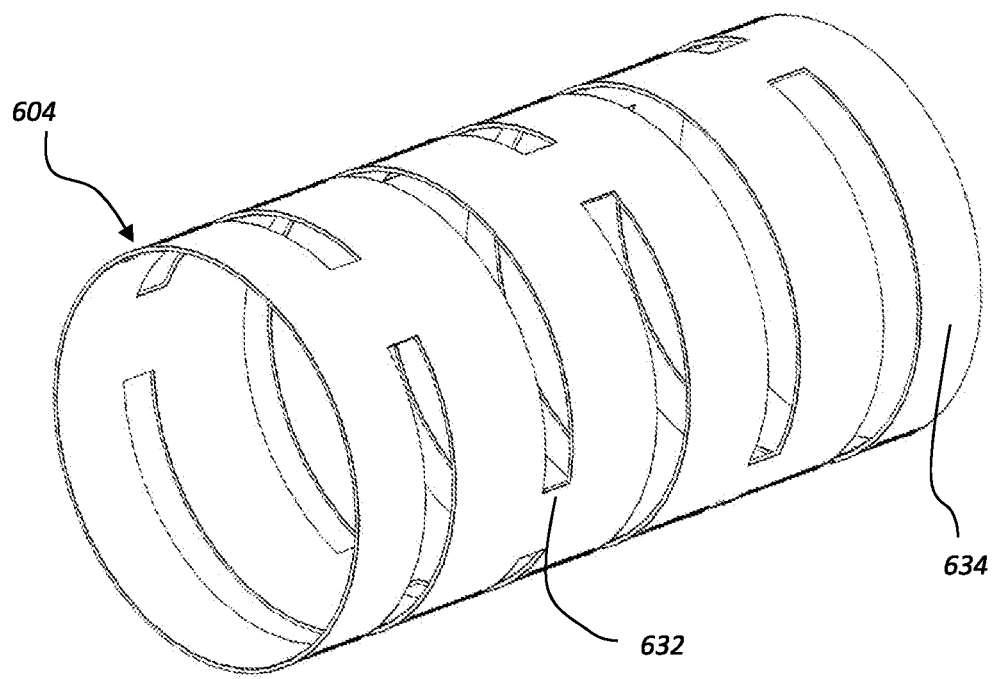
Figure 7:
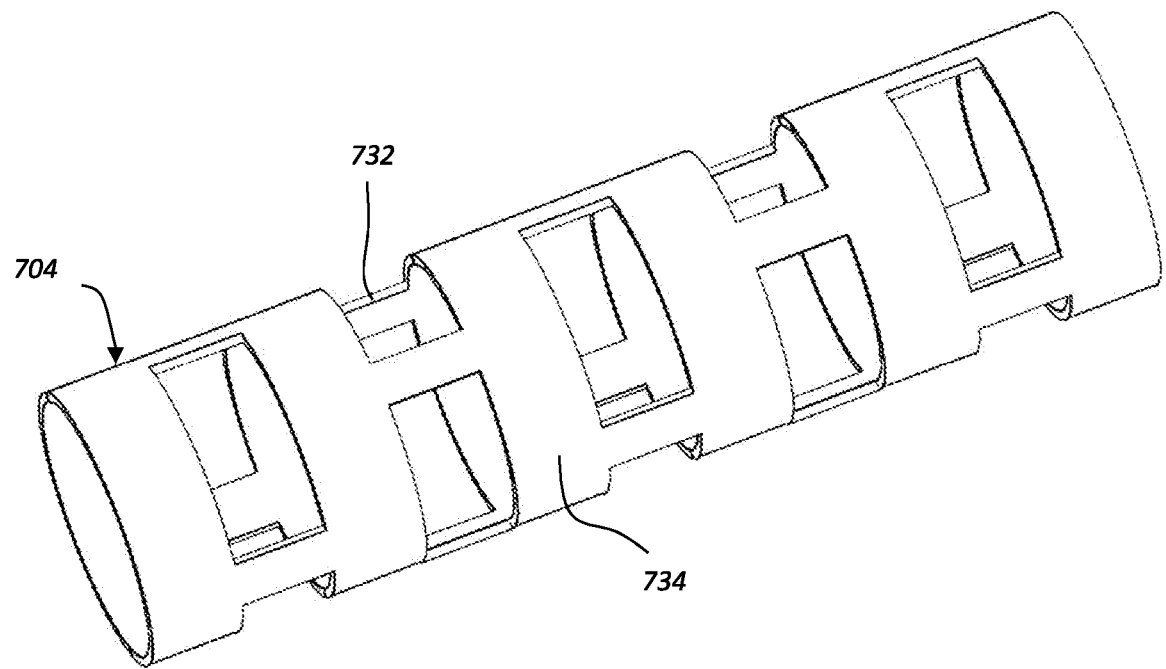

Cut patterns are referred to herein according to the number of axially extending beams disposed between each pair of adjacent circumferentially extending rings. FIGS. 3 and 4 illustrate "one-beam" cut patterns, FIGS. 5 and 6 illustrate "two-beam" cut patterns, and FIG. 7 illustrates a "three-beam" cut pattern. Other embodiments may include more than three beams between each pair of adjacent rings (e.g., a four-beam cut pattern, five-beam cut pattern, etc.).

The tube structure 304 illustrated in FIG. 3 includes a single beam 332 disposed between each pair of adjacent rings 334. Pairs of adjacent beams may alternate by 180 degrees, as shown. Additionally, or alternatively, sections may include beams positioned on a single side along a length of the tube, as shown by the beams 432 and rings 434 of the tube 404 of FIG. 4.

The tube structure 504 illustrated in FIG. 5 includes a pair of circumferentially opposing beams 532 disposed between each pair of adjacent rings 534. The corresponding beams 532 in each pair may be symmetrically circumferentially spaced (i.e., by about 180 degrees) as shown by FIG. 5. Alternatively, the corresponding beams may be circumferentially non-symmetric, as shown by the beams 632 and rings 634 of the tube 604 of FIG. 6. The tube structure 704 illustrated in FIG. 7 includes a triad of beams 732 disposed between each pair of adjacent rings 734. The corresponding beams in each triad may be symmetrically circumferentially spaced (i.e., by about 120 degrees) as shown, or may be positioned according to some non-symmetric arrangement.

Generally, the higher the number of beams left between each pair of adjacent rings, the relatively greater the stiffness of the tube. Cut patterns may therefore be selected to provide a desired flexibility profile along the length of the tube. Cut spacing, width, and/or depth may also be varied to provide desired flexibility characteristics. For example, one tube configuration can include a proximal section with relatively lower flexibility and relatively higher torquability that rapidly progresses to a distal section with relatively higher flexibility and relatively lower torquability. Beneficially, the flexibility provided by such cut patterns can minimize or prevent the tube from deforming the shape of the internal structures of the guidewire (e.g., the core) so that a customized shape of the tip can be better formed and maintained.

A section of tube having a two-beam cut pattern with substantially circumferentially equally spaced beams (as in FIG. 5) will typically have relatively higher ability to transmit torque and relatively lower flexibility, while a section of tube having non-symmetrically spaced beams (as in FIG. 6) will typically have a torque transmissibility and flexibility between that of a symmetrically spaced beam pattern and a one-beam pattern. The less circumferentially symmetric the corresponding pair of beams are positioned, the closer together circumferentially the resulting beams will be, and therefore the more similar the non-symmetric two-beam cut will be to a one-beam cut pattern. Such a non-symmetric two-beam pattern may therefore be used as a transition between a symmetric two-beam pattern and a one-beam pattern.

The cut patterns may form "segments" of repeating structural units along a length of the tube. In a typical one-beam embodiment, a single segment can be defined as a first beam 332 disposed between two adjacent rings 334 (one proximal ring and one distal ring) and a second opposing beam 332 extending from the distal ring and being rotationally offset by about 180 degrees from the first beam 332. Likewise, in a typical two-beam embodiment, a single segment can be defined as a first pair of beams 532 disposed between two adjacent rings 534 (one proximal ring and one distal ring) and a second pair of beams 532 extending from the distal ring and being rotationally offset from the first pair of beams by about 90 degrees. Likewise, in a typical three-beam embodiment, a single segment can be defined as a first triad of beams 732 disposed between two adjacent rings 734 (one proximal ring and one distal ring) and a second triad of beams 732 extending from the distal ring and being rotationally offset from the first triad by about 60 degrees.

Figure 8:
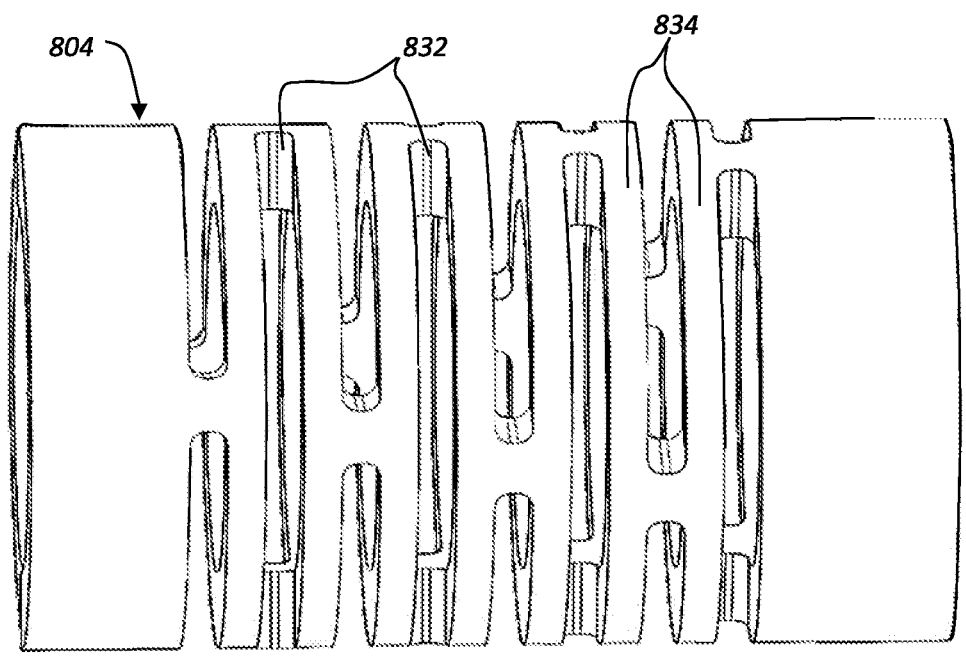

FIG. 8 illustrates a tube 804 having a plurality of beams 832 and rings 834. The illustrated cut pattern includes a rotational offset applied at each successive segment of the tube 804 to minimize preferred bending directions in the tube. As used herein, a "rotational offset" is the angular rotation between two adjacent segments. A rotational offset is therefore applied from one segment to the next, even though individual cuts within a segment may also be offset from one another.

As shown, the cuts may be arranged to form a substantially consistent rotational offset from one segment to the next. The illustrated cut pattern shows a rotational offset of about 5 degrees from one segment to the next. When multiple successive segments having such an angular offset are formed, the resulting pattern of beams along a sufficient length of the tube 804 wraps around the axis of the tube 804 in a continuously rotating helical pattern. The angular offset may be about 5, 15, 30, 45, 60, 75, 80, or 85 degrees. In some embodiments, the angular offset is applied at each successive segment. In other embodiments, a plurality of successive segments are disposed next to one another without an offset before the angular offset is applied.

The illustrated example shows a two-beam cut pattern with a series of rotational offsets. It will be understood, however, that the same principles may be applied to other cut patterns, such as a one-beam cut pattern, three-beam cut pattern, or cut pattern having greater than three beams per pair of adjacent rings. In preferred embodiments, each successive cut or sets of cuts (e.g., every second cut, third, fourth, etc.) along the length of a given section is rotationally offset by about 1, 2, 3, 5, or 10 degrees, or is offset by about 1, 2, 3, 5, or 10 degrees off from 180 degrees in a one-beam pattern, 1, 2, 3, 5, or 10 degrees off from 90 degrees in a two-beam pattern, 1, 2, 3, 5, or 10 degrees off from 60 degrees in a three-beam pattern, and so on for patterns having a higher beam count. These rotational offset values have beneficially shown good ability to eliminate flexing bias.

The separate components and features of the cut patterns shown in FIGS. 3 through 8 may be combined to form different tube configurations. For example, some tubes may be configured so as to have a section of two-beam cuts which transitions to a section of one-beam cuts.

Tip Variations

Figure 9:
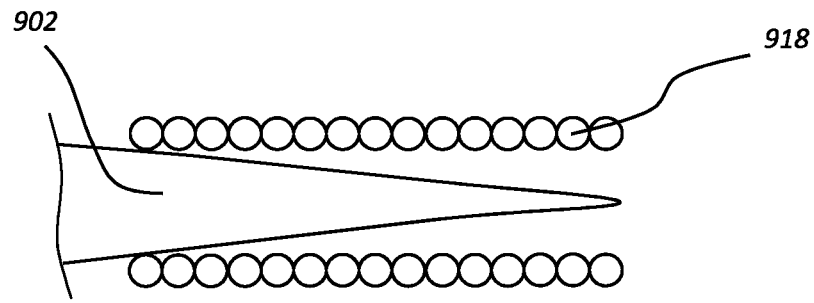
FIGS. 9 through 11 illustrate various distal tip configurations that may be utilized with the guidewire device.
Figure 10:
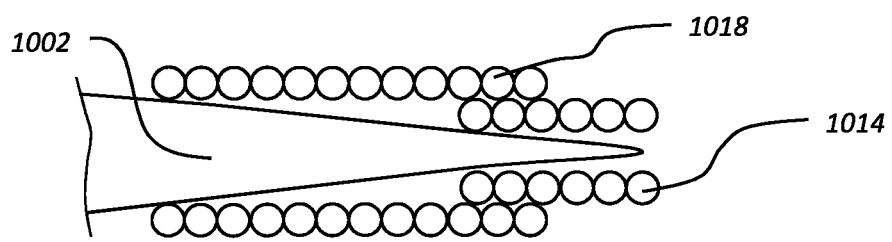
Figure 11:
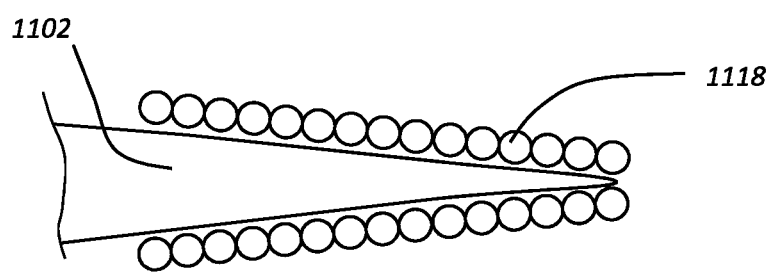

FIGS. 9 through 11 illustrate embodiments of various distal tip configurations that may be utilized with one or more of the embodiments described herein. FIG. 9 illustrates a continuous diameter tip configuration. Where the coil 918 surrounding the tapering core 902 has a substantially continuous diameter. FIG. 10 illustrates a stepped tip configuration where an outer coil 1018 positioned over the core 1002 has a substantially continuous diameter. A smaller diameter inner coil 1014 is positioned so as to extend further distally than the outer coil 1018 to provide a step-wise change in diameter of the tip. FIG. 11 illustrates a tapered tip configuration where the coil 1118 is tapered so as to match a taper of at least a portion of the core 1102. The tip embodiments illustrated in FIGS. 9 through 11 may be combined with any of the guidewire device embodiments described herein. For example, a desired tip configuration may be selected so as to provide desired shapeability and/or flexibility characteristics for a given guidewire application.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a tube section of any of FIGS. 3 through 8 and/or any element described in relation to a tip configuration of any of FIGS. 9 through 11 may be combined and used with the guidewire device of FIGS. 1 and 2. In any of the foregoing combinations, the distal tip of the core wire may be rounded, flat, or another shape.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A guidewire device having a shapeable tip, the guidewire device comprising:
   a core having a proximal section and a distal section, the distal section having a smaller diameter than the proximal section;
   a tube structure coupled to the core such that the distal section of the core passes into the tube structure and passes distally beyond the tube structure to form the shapeable tip; and
   one or more coils encompassing at least a portion of the tip, the one or more coils including
      an outer coil coupled to a distal end of the tube structure and extending distally from the tube structure, and
      an inner coil disposed at least partially within the tube structure so as to be positioned between an outer surface of the core and an inner surface of the tube structure, the inner coil being configured in size and shape to abut both an outer surface of the core and an inner surface of the tube structure, the inner coil also extending distally beyond the tube structure, wherein the outer coil encompasses at least a portion of the inner coil extending distally beyond the tube structure.

2. The guidewire device of claim 1, wherein the distal section of the core tapers from the proximal section of the core.

3. The guidewire device of claim 1, wherein the shapeable tip extends distally beyond the tube a distance of about 0.5 cm to 5 cm, or about 1 cm to 3 cm.

4. The guidewire device of claim 1, wherein the outer coil is formed from a material that is more plastically deformable than nitinol.

5. The guidewire device of claim 4, wherein the outer coil is formed from stainless steel.

6. The guidewire device of claim 1, wherein the inner coil is formed from a radiopaque material.

7. The guidewire device of claim 6, wherein the inner coil is formed from platinum.

8. The guidewire device of claim 1, wherein the tube structure is formed from nitinol.

9. The guidewire device of claim 1, wherein the core is formed from stainless steel.

10. The guidewire device of claim 1, wherein the tube structure includes a plurality of fenestrations defining a plurality of axially extending beams coupling a plurality of circumferentially extending rings.

11. The guidewire device of claim 10, wherein the plurality of fenestrations are arranged into one or more of a one-beam cut pattern, two-beam cut pattern, or three beam-cut pattern.

12. The guidewire device of claim 10, wherein the fenestrations define a cut pattern having a rotational offset such that each successive segment along a length of the tube structure are circumferentially rotated from a previous segment.

13. The guidewire device of claim 10, wherein the fenestrations define a cut pattern with cuts of increasing depth toward a distal end of the tube structure and/or with spacing between successive cuts that decreases toward a distal end of the tube structure.

14. The guidewire device of claim 1, wherein the inner coil is formed from a radiopaque material and the outer coil is formed from a non-radiopaque material.

15. The guidewire device of claim 14, wherein the non-radiopaque material is stainless steel.

16. The guidewire device of claim 1, wherein the inner coil and the outer coil are formed from different materials.

17. A guidewire device having a shapeable tip, the guidewire device comprising:
   a core having a proximal section and a distal section, the distal section having a smaller diameter than the proximal section;
   a tube structure coupled to the core such that the distal section of the core passes into the tube structure and passes distally beyond the tube structure to form the shapeable tip, wherein the tube structure includes a plurality of fenestrations defining a plurality of axially extending beams and circumferentially extending rings;
   an inner coil encompassing at least a portion of the distal section of the core, a portion of the inner coil being disposed so as to abut both an outer surface of the core and an inner surface of the tube structure, and a portion of the inner coil extending distally beyond the tube structure to form at least a portion of the tip; and
   an outer coil coupled to a distal end of the tube structure and extending distally from the tube structure, the outer coil encompassing the portion of the inner coil extending distally beyond the tube structure.

18. The guidewire device of claim 17, wherein the inner coil and the outer coil are configured such that the core at the tip is not subjected to an overriding recovery force.

19. A guidewire device having a shapeable tip, the guidewire device comprising:
   a core having a proximal section and a distal section, the distal section having a smaller diameter than the proximal section;
   a tube structure coupled to the core such that the distal section of the core passes into the tube structure and passes distally beyond the tube structure to form the shapeable tip; and
   one or more coils encompassing at least a portion of the tip, the one or more coils including
      an outer coil coupled to a distal end of the tube structure and extending distally from the tube structure, and
      an inner coil disposed at least partially within the tube structure and extending distally beyond the tube structure, wherein the outer coil encompasses at least a portion of the inner coil extending distally beyond the tube structure,
      wherein the inner coil extends farther distally than the outer coil.

20. A guidewire device having a shapeable tip, the guidewire device comprising:
- a core having a proximal section and a distal section, the distal section having a smaller diameter than the proximal section;
- a tube structure coupled to the core such that the distal section of the core passes into the tube structure and passes distally beyond the tube structure to form the shapeable tip; and
- one or more coils encompassing at least a portion of the tip, the one or more coils including
  - an outer coil coupled to a distal end of the tube structure and extending distally from the tube structure, and
  - an inner coil disposed at least partially within the tube structure and extending distally beyond the tube structure, wherein the outer coil encompasses at least a portion of the inner coil extending distally beyond the tube structure,
  - wherein the inner coil includes different sections each formed from different materials.

21. The guidewire device of claim 20, wherein a section of the inner coil extending distally beyond the tube structure is formed from a first material, and wherein a section of the inner coil within the tube structure is formed from a second, different material.

* * * * *